(12) United States Patent
Lee (10) Patent No.: US 11,160,976 B2
(45) Date of Patent: Nov. 2, 2021

(54) SKIN TREATMENT DEVICE USING NEEDLES

(71) Applicant: EUNSUNG GLOBAL CORP., Seoul (KR)

(72) Inventor: Ki Se Lee, Seoul (KR)

(73) Assignee: EUNSUNG GLOBAL CORP., Wonju-si (KR)

( * ) Notice: Subject to any disclaimer, the term of this patent is extended or adjusted under 35 U.S.C. 154(b) by 92 days.

(21) Appl. No.: 16/289,231

(22) Filed: Feb. 28, 2019

(65) Prior Publication Data

US 2019/0192850 A1  Jun. 27, 2019

Related U.S. Application Data

(63) Continuation-in-part of application No. 14/787,239, filed as application No. PCT/KR2015/004002 on Apr. 22, 2015, now abandoned.

(30) Foreign Application Priority Data

Feb. 17, 2015  (KR) .......................... 1020150024322

(51) Int. Cl.
  *A61N 1/32*  (2006.01)
  *A61N 1/20*  (2006.01)
  (Continued)

(52) U.S. Cl.
  CPC ............... *A61N 1/328* (2013.01); *A61M 5/20* (2013.01); *A61M 5/3298* (2013.01);
  (Continued)

(58) Field of Classification Search
  CPC ........ A61N 1/328; A61N 1/0502; A61N 1/20; A61N 1/306; A61N 1/0412; A61M 5/20;
  (Continued)

(56) References Cited

U.S. PATENT DOCUMENTS 5,869,326 A  2/1999 Hofmann
6,120,493 A  9/2000 Hofmann
(Continued)

FOREIGN PATENT DOCUMENTS

| KR | 10-2011-0104529 A | 7/2012 |
| KR | 10-1192764 B1 | 10/2012 |
| KR | 10-2012-0027604 A | 9/2013 |
| KR | 10-2014-0086275 A | 7/2014 |
| KR | 10-1489397 B1 | 2/2015 |

*Primary Examiner* — Catherine M Voorhees
*Assistant Examiner* — Roland Dinga
(74) *Attorney, Agent, or Firm* — Greer, Burns & Crain, Ltd (57) ABSTRACT

A skin treatment device is provided, which includes a needle frame in which a front end outlet of a needle that penetrates an inside thereof projects toward a front thereof, a rear end inlet of the needle is open to an outside of a rear surface thereof, and a stepped partition wall is provided in a closed shape on the outside of the rear surface thereof; a needle cover having a space portion formed on a rear thereof toward an inside thereof, a needle guide portion formed on a front surface thereof; a contact PCB configured to receive a power that is supplied from a power supply device; and a needle hub having an insertion portion formed in a front thereof toward an inside thereof.

11 Claims, 5 Drawing Sheets

(51) Int. Cl.
    *A61N 1/05*          (2006.01)
    *A61M 5/32*         (2006.01)
    *A61N 1/30*          (2006.01)
    *A61M 5/20*         (2006.01)
    A61N 1/04          (2006.01)
    A61M 5/46         (2006.01)

(52) U.S. Cl.
CPC ............ *A61N 1/0502* (2013.01); *A61N 1/20* (2013.01); *A61N 1/306* (2013.01); *A61N 1/327* (2013.01); *A61M 5/46* (2013.01); *A61M 2005/206* (2013.01); *A61N 1/0412* (2013.01)

(58) Field of Classification Search
CPC . A61M 5/3298; A61M 5/46; A61M 2005/206
See application file for complete search history.

(56) References Cited

U.S. PATENT DOCUMENTS

| | | |
|---|---|---|
| 2004/0176732 A1 | 9/2004 | Frazier et al. |
| 2008/0058706 A1 | 3/2008 | Zhang et al. |
| 2008/0200883 A1 | 8/2008 | Tomono |
| 2010/0030152 A1* | 2/2010 | Lee .................. A61M 37/0015 604/131 |
| 2013/0096602 A1 | 4/2013 | Kumar |
| 2013/0102954 A1* | 4/2013 | Choi ...................... A61H 39/08 604/21 |
| 2014/0066864 A1 | 3/2014 | Eum |
| 2017/0182303 A1* | 6/2017 | Tallarida ............... A61M 39/22 |

\* cited by examiner

SKIN TREATMENT DEVICE USING NEEDLES

CROSS-REFERENCE TO RELATED APPLICATIONS

This Application is Continuation-in-Part of, and claims 35 USC 120 priority from, U.S. Ser. No. 14/787,239 filed Oct. 26, 2015, which is a Section 371 National Stage Application of International Application No. PCT/KR2015/004002, filed on Apr. 22, 2015, the contents of which is hereby incorporated by reference in its entirety.

BACKGROUND

The present invention relates to a skin treatment device using needles used for electroporation therapy (EPT) to increase permeation of cells.

A human skin tissue is composed of a cornified layer, an epidermis layer, a dermis layer, and a hypodermis layer, and the function of a skin deteriorates due to aging and ultraviolet (UV) actions.

Representative changes of a skin due to aging and UV actions may include wrinkle creation due to reduction and deformation of a collagen tissue in a dermis, reduction of skin elasticity due to deformation of an elastic fiber that is composed of elastine, and melanin pigmentation according to activation of tyrosinase that exists in the epidermis layer.

As a method capable of raising a biological change by means of an efficacy material to prevent skin aging and to maintain and improve skin elasticity, there is a drug application method using the principle of electroporation that is called an electric perforation method.

The drug application method using the principle of electroporation has been mainly used for skin beauty, plastic surgical operation, and treatment of a specific body region. According to the drug application method, materials having predetermined molecular weights (equal to or lower than 4000 Dalton) permeate through a cell membrane in a manner that an electrical pulse that is applied to a skin upsets a phospholipid bilayer to temporarily make a hole on a skin surface, and drug flows into cells through the hole.

The hole that is created by the electrical pulse is closed at a moment when the applying of the electrical pulse is stopped, and the surgical operation using this is the electroporation. The electroporation has been used as a non-chemical method capable of transferring not only DNA in a live cell but also external materials having various kinds of molecular weights without changing the biological structure and function of the cell. A prior art related to the electroporation has already been disclosed in Korean Registered Patent No.

However, the prior art method that makes the necessary drug permeate into the cells by making an electrode plate for applying the electrical pulse to the skin contact the skin has the drawback that the drug efficacy arrives at the epidermis layer and the dermis layer through the cornified layer with low arrival rate. Although formulation or chemical skin absorption enhancers are used to improve the skin permeation rate, unsatisfactory results may be produced in the case where the drug is hydrophilic or the molecular weight is higher than 300 Dalton.

SUMMARY

Technical Problem

The present invention has been made to solve the above-mentioned problems occurring in the prior art while advantages achieved by the prior art are maintained intact.

One subject to be achieved by the present invention is to provide a needle electroporator, which is configured to make drug applied to cells through needles after forming a hole by upsetting a phospholipid bilayer through application of a high DC voltage to the needles, and thus can make an accurate amount of the drug applied to a person being surgically operated with an accurate depth to maximize efficacy of the drug.

Technical Solution

In one aspect of the present invention, there is provided a skin treatment device, which includes a needle frame in which a front end outlet of a needle that penetrates an inside thereof projects toward a front thereof, a rear end inlet of the needle is open to an outside of a rear surface thereof, and a stepped partition wall is provided in a closed shape on the outside of the rear surface thereof so that the rear end inlet of the needle is positioned inside the partition wall; a needle cover having a space portion formed on a rear thereof toward an inside thereof, a needle guide portion formed on a front surface thereof to communicate with the space portion and penetrated by the needle, and an insertion portion formed on a bottom surface thereof; a contact PCB configured to receive a power that is supplied from a power supply device, provided with a contact hole penetratingly formed on a front surface thereof so that the needle can penetrate the contact hole, and configured to apply positive electricity or negative electricity according to the power supply to the needle that penetrates the contact hole; and a needle hub having an insertion portion formed in a front thereof toward an inside thereof, an injection portion formed on an outside of a rear surface thereof to be connected to a syringe, and a path provided on an inside of the rear surface thereof to communicate with the insertion portion and to be inserted into an inside of the partition wall of the needle frame that is positioned inside the insertion portion, so that one front portion thereof is inserted into and coupled to the space portion of the needle cover in a state where the contact PCB and the needle frame are successively provided inside the partition wall of the needle frame.

In another aspect of the present invention, there is provided a skin treatment device, which includes a needle frame in which front end outlets of a plurality of needles that penetrate an inside thereof project toward a front thereof, rear end inlets of the needles are open to an outside of a rear surface thereof, and a stepped partition wall is provided in a closed shape on the outside of the rear surface thereof so that the rear end inlets of the needles are together positioned inside the partition wall; a needle cover having a space portion formed on a rear thereof toward an inside thereof, a plurality of needle guide portions formed on a front surface thereof to communicate with the space portion and respectively penetrated by the needles, and an insertion portion formed on a bottom surface thereof; a contact PCB configured to receive a power that is supplied from a power supply device, provided with a plurality of contact holes penetratingly formed on a front surface thereof so that the needles can penetrate the contact holes, and configured to apply positive electricity or negative electricity according to the power supply to the needles that penetrate the contact holes; and a needle hub having an insertion portion formed in a front thereof toward an inside thereof, an injection portion formed on an outside of a rear surface thereof to be connected to a syringe, and a path provided on an inside of the rear surface thereof to communicate with the insertion portion and to be inserted into an inside of the partition walls of the needle frame that is positioned inside the insertion portion, so that one front portion thereof is inserted into and coupled to the space portion of the needle cover in a state where the contact PCB and the needle frame are successively provided inside the partition walls of the needle frame.

A through-hole may be formed on an upper surface of the rear of the needle cover, a fastening hole may be formed on an upper surface of the front of the needle hub that is inserted into the space portion of the needle cover, and the through-hole and the fastening hole, which coincide with each other, may be fastened by a fastening means.

The skin treatment device according to the aspect of the present invention may further include an operation gun including a fixing portion formed on one side of an upper portion thereof to fix the insertion portion of the needle cover thereto; an operation portion which is formed on the other side of the upper portion thereof and to which a piston of the syringe that is coupled to the injection portion of the needle hub is fixed so that the operation portion moves the piston in forward and backward directions; a coupling portion provided between the fixing portion and the operation portion of the upper portion thereof to be coupled to a body of the syringe; and an operation gun having a handle provided on a lower portion thereof that is integrally formed with an upper portion thereof.

The insertion portion of the needle cover may be configured to close with an elastic force.

The coupling portion of the operation gun may close or widen in accordance with a forward or backward rotation of an adjustment portion to adjust a grasping force for fixing the body of the syringe.

The plurality of needles of the needle frame may be arranged in a center portion and radially on an outside around the center portion.

The path of the needle hub that is inserted into the inside of the partition wall of the rear surface of the needle frame may be configured to correspond to a shape of the partition wall, and the partition wall and the path are coupled to each other with a seal therebetween maintained.

The positive electricity may be applied to the needle that penetrates through the contact hole arranged in the center portion, and the negative electricity may be applied to the remaining needles that penetrate through the contact holes arranged on the outside around the center portion.

The negative electricity may be applied to the needle that penetrates through the contact hole arranged in the center portion, and the positive electricity may be applied to the remaining needles that penetrate through the contact holes arranged on the outside around the center portion.

A power supply portion for applying the power to the contact hole or the contact hole may include any one of a wire, a PFCB, a conductive spring, and a conductive spring pin.

The power that is supplied from the power supply device to the contact PCB may be an AC power or a DC power, or may have a sine or cosine waveform.

Advantageous Effect

According to the present invention as described above, when the drug is supplied from the syringe into the cells through the plurality of needles, high-voltage energy is transferred to the skin through the needles simultaneously or for an ultrashort time period in the unit of milliseconds. Accordingly, the surgical operation becomes simple, and time for the surgical operation can be shortened. Further, the drug which is hydrophilic or has giant molecular weight can easily permeate into the cells.

BRIEF DESCRIPTION OF THE DRAWINGS

The above objects, other features and advantages of the present invention will become more apparent by describing the preferred embodiments thereof with reference to the accompanying drawings, in which.

DETAILED DESCRIPTION

Hereinafter, a preferred embodiment of the present invention will be described with reference to the accompanying drawings. The matters defined in the description, such as the detailed construction and elements, are nothing but specific details provided to assist those of ordinary skill in the art in a comprehensive understanding of the invention, and thus the present invention is not limited thereto.

Further, the size or shape of constituent elements illustrated in the drawings may be exaggerated for clarity and convenience in explanation. Further, all terms used in the description are terms that are specially defined in consideration of their configurations and functions in the present disclosure may differ depending on intentions of a user or an operator or customs. Accordingly, they should be defined on the basis of the contents of the whole description of the present disclosure.

First, a needle electroporator according to the present invention includes a needle frame in which one or more needles are installed, a contact PCB coupled to a front of the needle frame to apply a voltage to the needles, a needle hub configured to accommodate the needle frame and the contact PCB, which are coupled to each other, therein and to transfer drug to the needles, and a needle cover to which the needle hub that accommodates the needle frame and the contact PCB is coupled from the rear of the needle cover. The details of the respective constituent elements as described above will be described with reference to FIG. 1.

Figure 1:
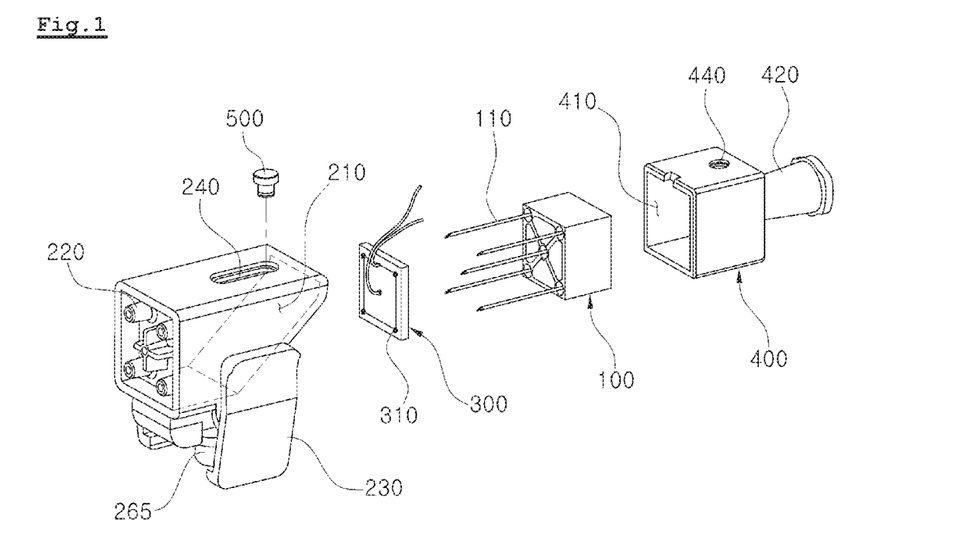
FIG. 1 is a partially exploded perspective view illustrating the configuration according to an embodiment of the present invention.

A needle frame 100 serves to fix a needle 110, and the needle 110 is penetratingly fixed in forward and backward directions of the needle frame 100. A front end of the needle 110 projects from the front of the needle frame 100 for a predetermined length, and a rear end of the needle 110 is positioned on the outside of a rear surface of the needle frame 100.

One or more needles 110 may be installed in the needle frame 100, and in the case where plural needles 110 are installed, they may be diversely arranged at predetermined intervals inside the needle frame 100.

In a preferred embodiment in which plural needles 110 are installed in the needle frame 100, one needle 110 may be positioned in the center of the needle frame 100, and the remaining needles 110 may be radially arranged along an outer circumference of the needle frame 100 around the needle 110 that is positioned in the center.

In another preferred embodiment in which plural needles 110 are installed in the needle frame 100, the cross section of the needle frame 100 may be in the form of a rectangle so that the needle frame 100 forms a hexahedron as a whole as shown in FIG. 1. In this case, one needle 110 may be positioned in the center of the needle frame 100, and the remaining needles 110 may be arranged at corner portions of the rectangle around the needle 110 that is positioned in the center.

On the outside of the rear surface of the needle frame 100, the rear ends of the needles 110 are positioned, and inlets 112 at the rear ends of the needles 110 are exposed to the outside of the rear surface of the needle frame 100, and outlets 111 at the front ends of the needles 110 project to the front of the needle frame 100.

On the surface of the outside of the rear surface of the needle frame 100, a partition wall 120 having a stepped portion is formed to project with a predetermined height. The partition wall 120 forms a closed loop on the surface of the outside, and the rear inlets of the needles 110 are positioned inside the closed partition wall 120. Accordingly, drug that flows into the partition wall 120 is injected simultaneously through the rear inlets 112 of the needles 110 that are positioned inside the partition wall 120.

Figure 4:
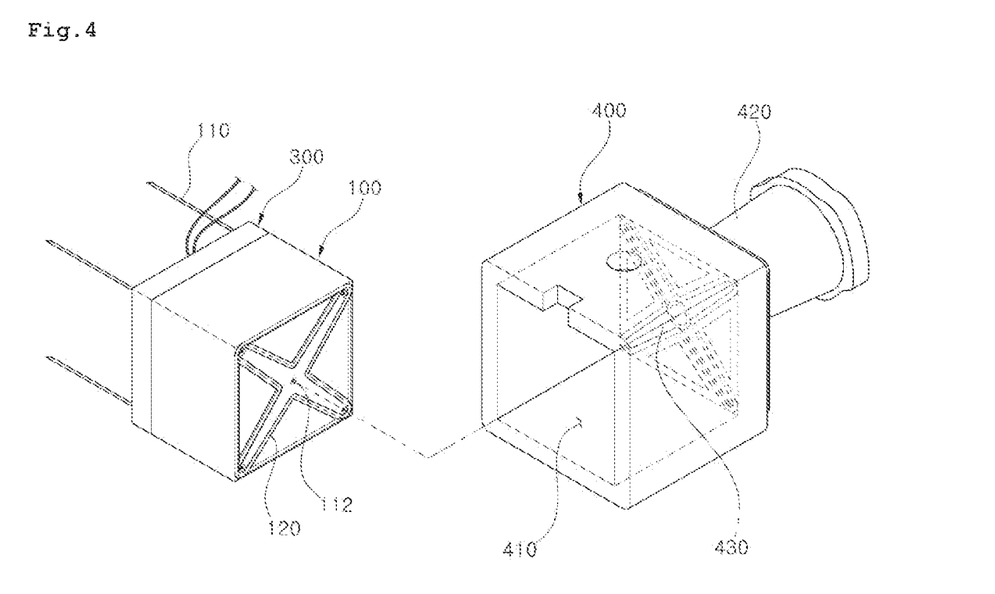
FIG. 4 is a view illustrating a state before a needle frame and a needle hub are coupled to each other according to an embodiment of the present invention.

It is not necessary to limit the shape of the partition wall 120, and as shown in FIG. 4, the partition wall 120 may be diversely formed in a closed loop so as to accommodate all the rear inlets 112 of the needles 110 that are provided in the needle frame 100.

The partition wall 120 may be integrally formed of the same material as the needle frame 100. If needed, the partition wall 120 may be formed of a soft material which has a buffering function differently from the material of the needle frame 100, and may be installed to be coupled to the outside of the rear surface of the needle frame 100.

The needle cover 200 is coupled to a needle hub 400 in a state where the above-described needle frame 100 and a contact PCB 300 to be described later are coupled to the needle hub 400.

Figure 5:
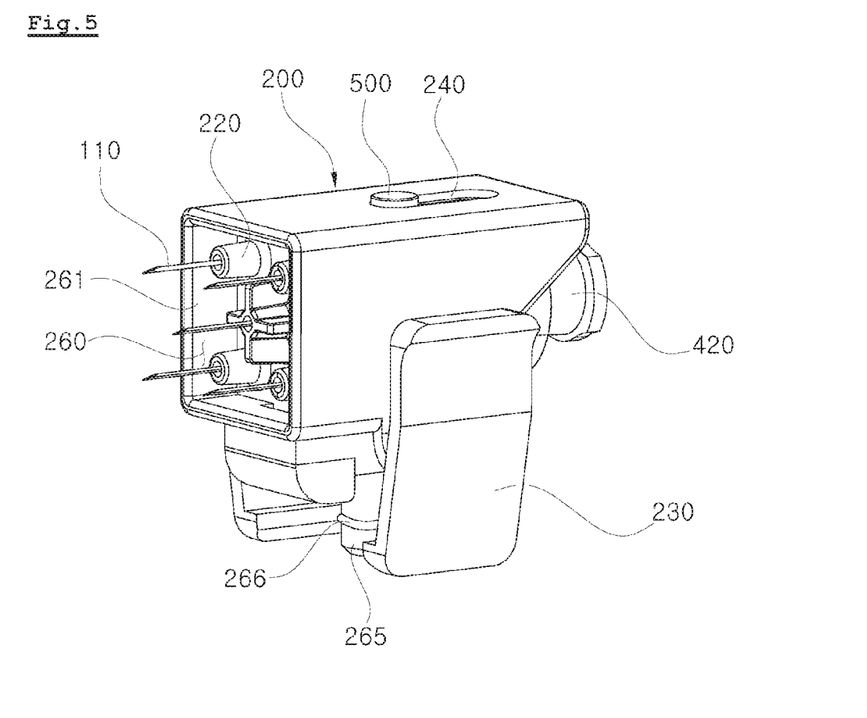
FIG. 5 is a perspective view illustrating a state where a contact PCB, a needle frame, and a needle hub are coupled to a needle cover according to an embodiment of the present invention.
Figure 6:
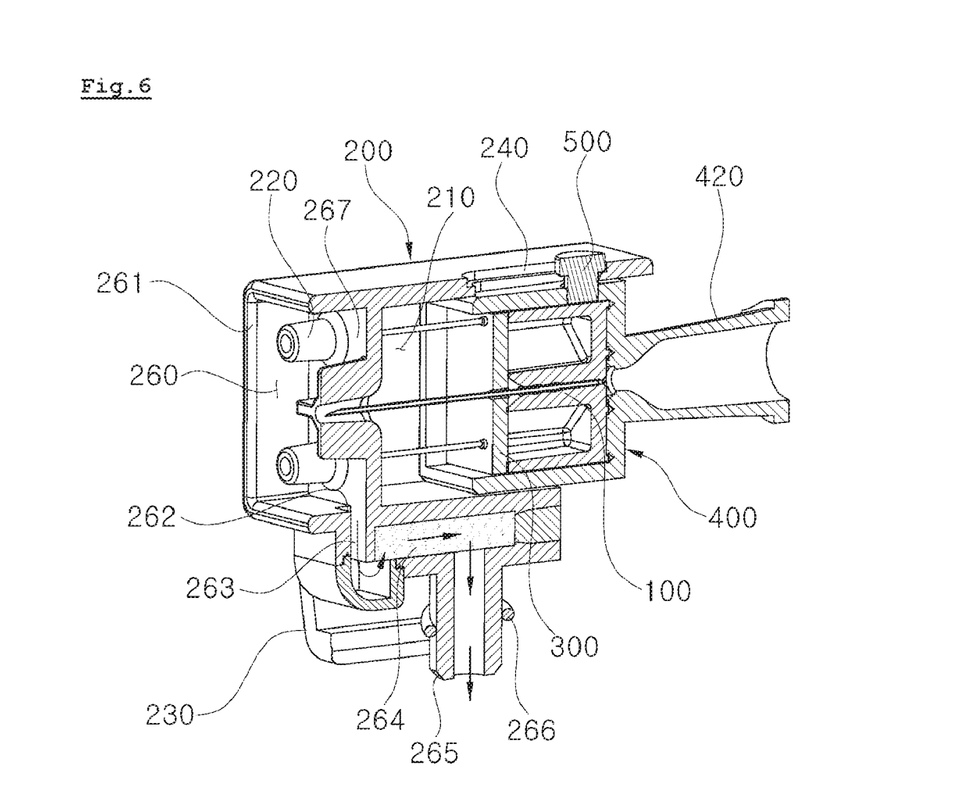
FIG. 6 is a cross-sectional view of FIG. 5.

As shown in FIGS. 5 and 6, the needle cover 200 is formed with a space portion 210 having a predetermined depth in the rear, and an opening 261 formed at the front thereof. A suction area 260 is formed by being enclosed by a plate 267 in the front of the needle cover 200 spaced apart from the opening 261.

At least one needle guide 220 is formed in the plate 267 so that the needle 110 can be penetrated and supported. A plurality of needle guides 220 are formed to face the suction area 260.

The needle frame 100 is coupled to the space portion 210 of the needle cover 200.

When the plurality of needles 110 are provided in the needle frame 100, the needle guide 220 is also formed in a number corresponding to the plurality of needles 110.

The arrangement of the needle guides 220 is also arranged to correspond to the needle 110 arranged in the needle frame 100.

An insertion portion 230 is formed on the bottom surface of the needle frame 100 so as to be fixed to an operation gun 700 to be described later.

The insertion portion 230 may be variously modified to allow the operation gun 700 to be fixed to the operation gun 700 through various fastening methods, such as a fastening scheme, a fastening scheme using a fastening means, or a hook-like hooking scheme.

In the embodiment of the present invention, as shown in FIG. 1, the insertion portion 230 is formed in a pair and in a plate shape formed on both sides of the bottom surface of the needle cover 200, so that both side plates are configured in a tightening manner having an elastic force.

When the upper ends of both of the insertion portion 230 are pushed inward, the lower ends of the insertion portions 230 are opened. In such a state, when the insertion portion 230 is positioned at the mounting site of the operation gun 700 and then the external force applied to the upper ends of both of the insertion portions 230 is removed, the needle cover 200 may be fixed to the operation gun 700 by retracting both lower ends of the opened insertion portions 230 through an elastic member not shown in the drawing.

On the other hand, a vacuum suction portion for exerting a suction force through the suction area 260 of the needle cover 200 is included.

A suction hole 262 is formed in the vacuum suction portion to communicate with the suction area 260 of the needle cover 200 and applies the suction force.

A suction passage 263 is formed in the vacuum suction portion of the needle cover 200, one end of the suction passage is connected to the suction hole 262.

The other end of the suction passage 263 is connected to a connection 265 to be connected to an external vacuum generating means (not shown).

The connection 265 protrudes in the shape of a tube formed on the outer side of the needle cover 200 and a packing 266 for maintaining airtightness is formed on the outer circumferential surface thereof.

The suction passage 263 connects the suction hole 262 and the connection 265. A filter 264 is installed in the suction passage 263 so that the inhaled drug and blood may not be introduced into the vacuum generating means.

Therefore, the vacuum generating means is prevented from being contaminated by drugs and blood and kept clean.

The contact PCB 300 is a printed circuit board that applies positive or negative voltage to the contact holes 310 through a power that is supplied from a power supply device (not illustrated in the drawing).

The power supply device may operate in an external power mode or in an internal power mode. The external power mode is a mode in which the power supply device uses an external power through reception of commercialized voltages for home or industry, and in the external power mode, a voltage may be received from an outside through a DC adaptor arranged at one end of the power supply device.

The internal power mode is a mode in which an external power that is received through a DC adaptor is charged in the power supply device, and in the internal power mode, the stored power is provided even without connection to the outside through wires to improve portability.

The voltage that is applied to the contact PCB is used to make a pulse that is applied for reversible poration of a cell membrane, and the pulse may be unipolar, bipolar, or logarithmic, and further may be in the form of square waves or other waves. The pulse is determined in accordance with the property of a cell tissue, the size and the position of the selected cell tissue so as to raise an electric perforation in a specific place in a body tissue, and includes uniform and sufficient voltage, current, density, duration time, and pulse frequency.

A pulse generation device may generate an electric pulse having an average voltage of 1 to 200 V.

The pulse generation device may generate an electric pulse having current in the range of 1 mAmp to 400 mAmp.

Preferably, the pulse generation device may be configured to provide a current range selected from the group including 10 to 40 mAmp, 25 to 100 mAmp, 50 to 150 mAmp, 125 to 200 mAmp, 175 to 250 mAmp, 225 to 300 mAmp, and 300 to 400 mAmp.

The pulse generation device may have a frequency selected from the group including 1 to 10,000 Hz.

The pulse generation device may have a time length selected from the group including 0.1 µs to 1000 ms.

Figure 2:
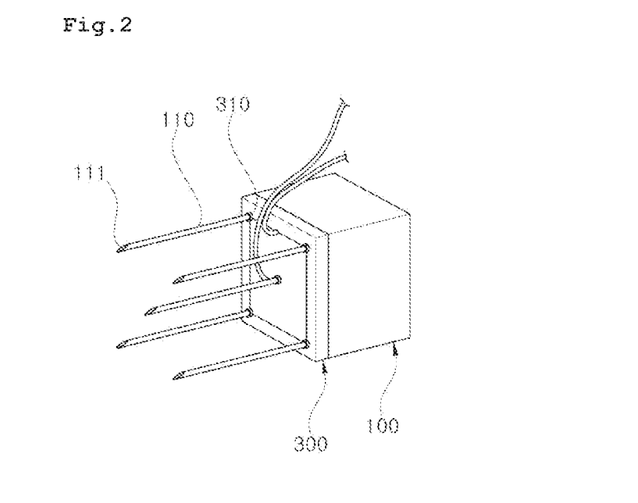
FIG. 2 is a perspective view illustrating a coupling state of a contact PCB and a needle frame according to an embodiment of the present invention.

According to the detailed structure of the contact PCB 300, one or more penetrated contact holes 310 are formed on the front surface of the contact PCB 300, and as shown in FIG. 2, the needles 110 of the needle frame 100 penetrate through the contact holes 310 to connect the needles 110 and the contact holes 310 to each other.

The number and the shape of the contact holes 310 that are formed on the contact PCB 300 correspond to the number of the needles 110 of the needle frame 100 and the arrangement shape of the needles 110 arranged in the needle frame 100.

The contact holes 310 may be connected to each other with diverse circuit patterns, and in a preferred embodiment in which the plurality of needles 110 are provided in the needle frame 100 as illustrated in FIG. 1, a positive voltage may be applied to the contact hole 310 that is put in the center, and a negative voltage may be applied to the contact holes 310 that are positioned at four corners to be connected to one another. If needed, a negative voltage may be applied to the contact hole 310 that is put in the center, and a positive voltage may be applied to the contact holes 310 that are positioned at four corners to be connected to one another.

The contact holes 310 and the power supply device may be connected by wires as shown in FIGS. 1 and 2, or may also be connected by a flexible FPCB, a conductive spring, or a conductive spring pin.

The contact PCB 300 is coupled to the front of the needle frame 100, and the front end of the needle that projects to the front of the needle frame 100 penetrates through the contact hole 310 of the contact PCB 300 to connect the needle 110 and the contact hole 310 to each other. For electrical connection, the needle 110 and the contact hole 310 may be fixed to each other by soldering or contact through interference fitting.

The power that is supplied to the contact PCB 300 may be an AC power or a DC power, or may have a sine or cosine waveform, and the frequency may be diversely injected as low frequency, middle frequency, and high frequency. Further, a stimulus pulse can be diversely varied.

Figure 3:
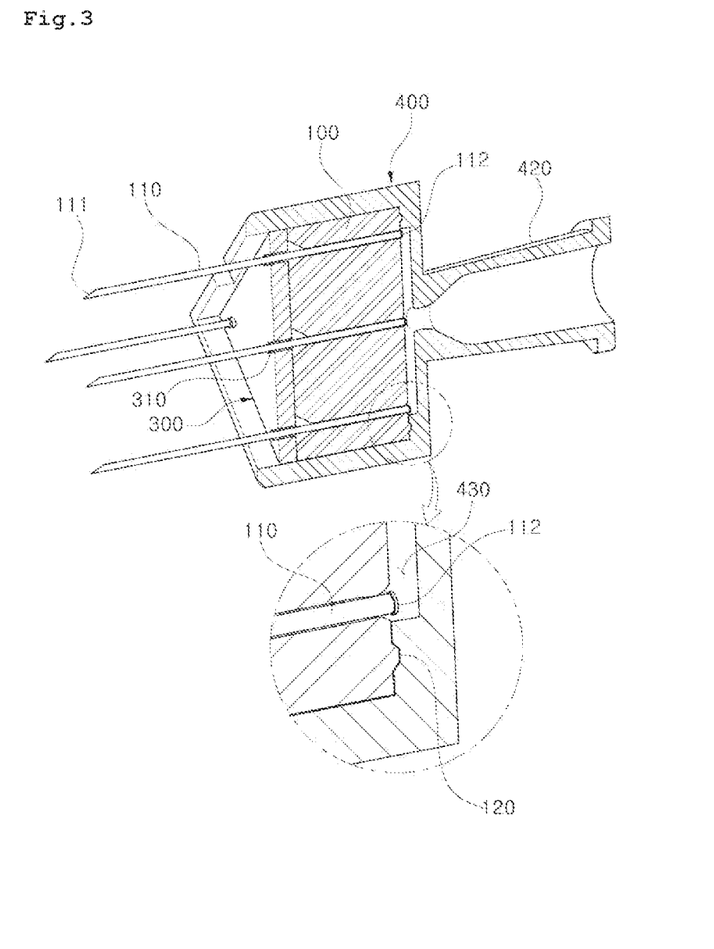
FIG. 3 is a cross-sectional view illustrating a coupling state of a needle frame and a needle hub according to an embodiment of the present invention.

As illustrated in FIGS. 1 and 3, the contact PCB 300 and the needle frame 100 are fixedly inserted into the needle hub 400, and then the needle hub 400 is inserted through the rear of the needle cover 200. On the front surface of the needle hub 400, an insertion portion 410 having a predetermine depth toward the inside is formed so that the contact PCB 300 and the needle frame 100 are inserted therein, and in the rear of the needle hub 400, an injection portion 420 that communicates with the insertion portion 410 is formed to project to the outside.

It is not required to limit the shape of the needle hub 400, but as illustrated in FIG. 1, the needle hub 400 may have a shape that corresponds to the needle frame 100. In addition, a part of the front of the needle hub 400 may be fixedly inserted into the space portion 210 of the needle cover 200 to correspond to the needle cover 200.

The injection portion 420 of the needle hub 400 may be configured to have a funnel shape having an inner diameter that is gradually narrowed as going toward the needle hub 400.

On an inside of the rear surface of the needle hub 400, a path 430, which has a center portion that communicates with the injection portion 420 and forms a closed loop as shown in FIG. 4, may be formed. The path 430 may be formed to project from the inside of the rear surface of the needle hub 400 to the outside thereof.

Accordingly, if the needle frame 100 is inserted into the insertion portion 410 of the needle hub 400, the partition wall 120 that is positioned on the outside of the rear surface of the needle frame 100 is coupled to the path 430 that is positioned inside of the rear surface of the needle hub 400. In this case, the partition wall 120 and the path 430 have shapes that correspond to each other, and the path 430 may be accommodated in and coupled to the inside of the partition wall 120, or the partition wall 120 may be accommodated in and coupled to the inside of the path 430. Accordingly, the path 430 of the needle hub 400 may be sealed up through coupling with the partition wall 120.

If the path 430 of the needle hub 400 and the partition wall 120 of the needle frame 100 are coupled to each other, as shown in FIG. 3, the drug that is supplied from the center of the path 430 through the injection portion 420 moves along the four paths 430, and thus the entire amount of the drug moves to the rear inlets 112 of the needles 110 inside the partition wall 120 that is coupled to the path 430 without being leaked to the outside.

The needle hub 400 is inserted into and coupled to the space portion 210 of the needle cover 200 in a state where the contact PCB 300 and the needle frame 100 are provided in the insertion portion 410 as shown in FIGS. 5 and 6. In this case, the needle hub 400 and the needle cover 200 are fastened to each other as follows. For example, if a part of the front surface of the needle hub 400 is inserted into the space portion 210 of the needle cover 200 in a state where a through-hole 240 is formed on the upper surface of the rear of the needle cover 200, and a fastening hole 440 is formed on the upper surface of the front of the needle hub 400, the through-hole 240 of the needle cover 200 and the fastening hole 440 of the needle hub 400 coincide with each other, and thus the through-hole 240 and the fastening hole 440, which coincide with each other, are fixed to each other through a fastening means 500. If the through-hole 240 of the needle cover 200 is formed as an elongated hole in the form of a slot, the fastening hole 440 can move in forward and backward directions within the range of the through-hole 240 during the fastening by the fastening means 500, and thus the insertion depth can be adjusted when the part of the front end of the needle hub 400 is inserted into the space portion 210 of the needle cover 200.

Figure 7:
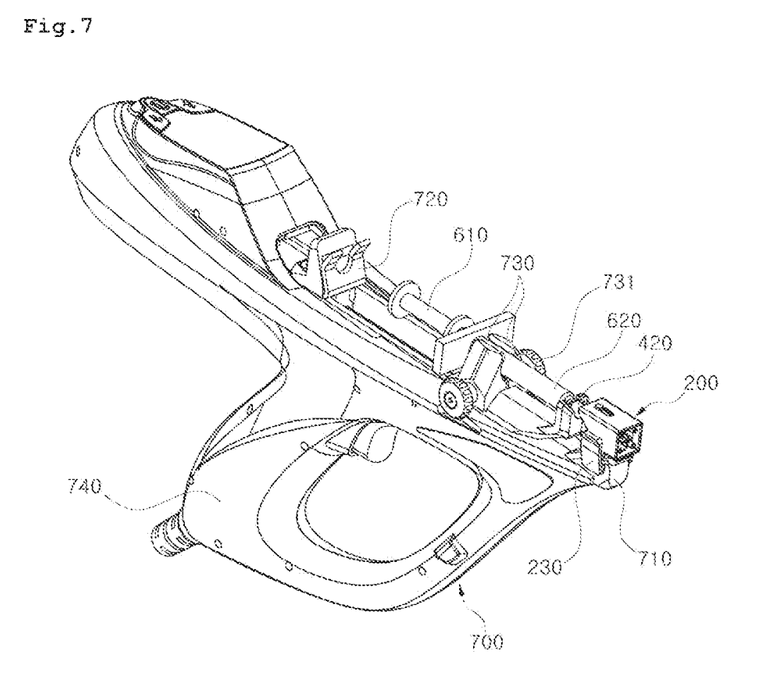
FIG. 7 is a perspective view illustrating an installation state of an operation gun in a state where a contact PCB, a needle frame, and a needle hub are coupled to a needle cover according to an embodiment of the present invention.

In a state where the needle cover 200, the contact PCB 300, the needle frame 100 having the needles 110, and the needle hub 400 are coupled to one another, a syringe 620 may be coupled to the injection portion 420 of the needle hub 400. In this case, the drug of the syringe 620 may be applied to a person being surgically operated through the needles 110 with the power supply to the contact PCB 300 through manual adjustment of a piston 610 of the syringe 620. However, as shown in FIG. 7, the drug can be stably and accurately applied to the person being surgically operated using an operation gun 700.

The operation gun 700 may include a fixing portion 710 formed on one side of an upper portion thereof, an operation portion 720 which is formed on the other side of the upper portion thereof and is coupled to the piston 610 of the syringe to move the piston 610 in the forward and backward directions, and a coupling portion 730 provided between the fixing portion 710 and the operation portion 720 to fix a body of the syringe 620.

A handle 740 may be provided on a lower portion thereof that is integrally formed or assembled with an upper portion of the operation gun 700 to extend downward, and an operation button (not illustrated in the drawing) may be provided on the handle 740.

A pair of coupling portions 730 of the operation gun 700 may be positioned on both sides that face each other around the body of the syringe 620 to fix the body of the syringe 620, and the coupling portions 730 may close or widen in accordance with rotation of an adjustment portion 731 that horizontally penetrates the lower side, so that the coupling portions 730 presses the body of the syringe 620 in stages to fix the body in accordance with the adjustment of the adjustment portion 730.

According to the needle electroporator according to the present invention, in a state where the contact PCB 300 and the needle frame 100 are coupled to each other and are provided in the needle hub 400, a portion of the front end of the needle hob 400 is fixedly inserted into the space portion 210 of the rear surface of the needle cover 200, and then as shown in FIG. 7, the insertion portion 230 of the needle cover 200 is fixedly inserted into the fixing portion of the operation gun 700. Further, the body of the syringe 620, in which the drug is stored, is coupled to the injection portion 420 of the needle hub 400, the body of the syringe 620 is coupled through the coupling portion 730 of the operation gun 700, and the piston 610 of the syringe 620 is fixed to the operation portion 720 of the operation gun 700.

Thereafter, if an operator pricks a treatment region of the person being surgically operated with the needles that project through needle guide portions 220 of the needle cover 200 using the operation gun 700 and then the positive electricity and the negative electricity are applied in accordance with the pattern of the contact holes 310 of the contact PCB 300 to which the power of the power supply device is applied, the skin of the person being surgically operated is perforated, and an accurate amount of the drug is applied into the skin of the person being surgically operated with an accurate depth.

INDUSTRIAL APPLICABILITY

The present invention can be used in a skin treatment device, which is configured to make drug applied to cells through needles after forming a hole by upsetting a phospholipid bilayer through application of a high DC voltage to the needles and thus can make an accurate amount of the drug applied to a person being surgically operated with an accurate depth to maximize efficacy of the drug.

While the present invention has been described in connection with the specific embodiments illustrated in the drawings, they are merely illustrative, and the invention is not limited to these embodiments. It is to be understood that various equivalent modifications and variations of the embodiments can be made by a person having an ordinary skill in the art without departing from the spirit and scope of the present invention. Therefore, the true technical scope of the present invention should not be defined by the above-mentioned embodiments but should be defined by the appended claims and equivalents thereof.

What is claimed is:
1. A skin treatment device comprising:
a plurality of needles;
a needle frame including a partition wall, said partition wall being configured to receive said plurality of needles, wherein at least a portion of said plurality of needles project from a front end of said needle frame, and wherein rear end inlets of said plurality of needles are positioned inside said partition wall and extend to a rear surface of said needle frame;
a needle cover having a front surface and defining a space portion, said needle cover including a plurality of needle guides formed on said front surface, said needle guides being in communication with the space portion and configured to receive said plurality of needles, said needle guide including an insertion portion formed on a bottom surface of said needle guide; wherein an opening is formed in the needle cover, the needle cover comprises:
a suction area formed to communicate with the opening; and
a vacuum suction portion for exerting a suction force to the suction area;
wherein the vacuum suction portion comprises: a suction hole formed to communicate with the suction area of the needle cover and apply a suction force;
a suction passage formed in the vacuum suction portion and connected to the suction hole; and a connection formed to communicate with the suction passage;
a contact PCB defining a plurality of contact holes, said plurality of contact holes being configured to receive power supplied from a power supply device and receive said plurality of needles and apply positive electricity or negative electricity according to the power supply to said plurality of needles;
a needle hub having an insertion portion and an injection portion formed on a rear surface of said needle hub, said injection portion being configured to be connected to a syringe, said needle hub having a rear surface defining a path that is in communication with the insertion portion and adjacent to the partition wall of the needle frame so that a front end of said needle hub is inserted into and coupled to the space portion of the needle cover in a state where the contact PCB and the needle frame are successively provided inside the partition wall of the needle frame,
wherein the path of the needle hub, which is adjacent to the partition wall of the rear surface of the needle frame, is configured with a shape that corresponds to a shape of the partition wall, and the partition wall and the path are coupled to each other such that a seal is formed between the partition wall and the needle hub, and
an operation gun that includes:
a fixing portion formed on a first end of the operation gun and configured to fix the insertion portion of the needle cover to the operation gun;
an operation portion formed on a second side of the operation gun and a piston of the syringe coupled to the injection portion of the needle hub so that the operation portion moves the piston in forward and backward directions;

a coupling portion provided between the fixing portion and the operation portion, wherein said coupling portion is coupled to a body of the syringe; and a handle provided on a lower portion of the operation gun.

2. The skin treatment device of claim 1, wherein a through-hole is formed on an upper surface of the needle cover and a fastening hole is formed on an upper surface of the needle hub, wherein the through-hole and the fastening hole are aligned with each other when the needle hub is inserted in the needle cover and configured to receive a fastening means to secure the needle hub and the need cover together.

3. The skin treatment device of claim 1, wherein the operation gun including a pair of the coupling portions, said pair of the coupling portions being positioned on opposing sides of the syringe, and comprising an adjusting hole threading horizontally through a lower portion of said pair of the coupling portions, said adjusting hole in the pair of the coupling portions being configured to receive an adjustment portion, wherein the coupling portions of the operation gun are moved between an open position and a retracted position based on rotation of the adjustment portion relative to the adjusting hole to adjust a gripping force on the syringe.

4. The skin treatment device of claim 1, wherein said plurality of needles are arranged in a center portion and radially around the center portion of the needle frame.

5. The skin treatment device of claim 4, wherein positive electricity is applied by the contact PCB to the needle of the plurality of needles arranged in the center portion, and negative electricity is applied by the contact PCB to the remaining needles of the plurality of needles that are arranged radially around the center portion.

6. The skin treatment device of claim 4, wherein negative electricity is applied by the contact PCB to the needle of the plurality of needles arranged in the center portion, and positive electricity is applied by the contact PCB to the remaining needles of the plurality of needles that are arranged radially around the center portion.

7. The skin treatment device of claim 1, wherein the power supply device configured for applying the power to the plurality of contact holes, comprises a wire, a conductive spring, and a conductive spring pin to connect the power supply device to the plurality of contact holes.

8. The skin treatment device of claim 1, wherein the power that is supplied from the power supply device to the contact PCB is an AC power, a DC power, or a sine waveform or a cosine waveform.

9. The skin treatment device of claim 1, further comprising:

a filter installed in the suction passage.

10. A skin treatment device comprising:

a plurality of needles;

a needle frame including a partition wall, said partition wall being configured to receive said plurality of needles, wherein at least a portion of said plurality of needles project from a front end of said needle frame, and wherein rear end inlets of said plurality of needles are positioned inside said partition wall and extend to a rear surface of said needle frame;

a needle cover having a front surface and defining a space portion, said needle cover including a plurality of needle guides formed on said front surface, said needle guides being in communication with the space portion and configured to receive said plurality of needles, said needle guide including an insertion portion formed on a bottom surface of said needle guide, wherein an opening is formed in the needle cover and the needle cover includes a suction area formed to communicate with the opening and a vacuum suction portion for exerting a suction force to the suction area, and wherein the vacuum suction portion comprises a suction hole formed to communicate with the suction area of the needle cover and apply a suction force, a suction passage formed in the vacuum suction portion and connected to the suction hole and a connection formed to communicate with the suction passage;

a contact PCB defining a plurality of contact holes, said plurality of contact holes being configured to receive power supplied from a power supply device and receive said plurality of needles and apply positive electricity or negative electricity according to the power supply to said plurality of needles; and a needle hub having an insertion portion and an injection portion formed on a rear surface of said needle hub, said injection portion being configured to be connected to a syringe, said needle hub having a rear surface defining a path that is in communication with the insertion portion and adjacent to the partition wall of the needle frame so that a front end of said needle hub is inserted into and coupled to the space portion of the needle cover in a state where the contact PCB and the needle frame are successively provided inside the partition wall of the needle frame, wherein the path of the needle hub, which is adjacent to the partition wall of the rear surface of the needle frame, is configured with a shape that corresponds to a shape of the partition wall, and the partition wall and the path are coupled to each other such that a seal is formed between the partition wall and the needle hub.

11. The skin treatment device of claim 10, further comprising a filter installed in the suction passage.

* * * * *